United States Patent [19]

Cohnen et al.

[11] Patent Number: 4,526,897
[45] Date of Patent: Jul. 2, 1985

[54] HYPERTENSIVE ISOINDOLIN-2-YL-AMINOIMIDAZOLINES AND ISOINDOLIN-2-YL-GUANIDINES

[75] Inventors: Erich Cohnen; Ben Armah, both of Hamburg, Fed. Rep. of Germany

[73] Assignee: Beiersdorf Aktiengesellschaft, Hamburg, Fed. Rep. of Germany

[21] Appl. No.: 407,972

[22] Filed: Aug. 13, 1982

[30] Foreign Application Priority Data

Aug. 22, 1981 [DE] Fed. Rep. of Germany ....... 3133302

[51] Int. Cl.³ .................. A61K 31/415; A61K 31/40; C07D 403/12; C07D 209/44
[52] U.S. Cl. .................................... 514/392; 514/416; 548/316; 548/348; 548/482
[58] Field of Search ........................ 548/316, 482, 348; 424/273 R, 274

[56] References Cited

U.S. PATENT DOCUMENTS 4,221,798 9/1980 Cohnen ........................... 548/316 X

FOREIGN PATENT DOCUMENTS 0000151 1/1979 European Pat. Off.
2816627 10/1979 Fed. Rep. of Germany ...... 548/316
2905501 8/1980 Fed. Rep. of Germany ...... 548/316
1014658 12/1965 United Kingdom .

OTHER PUBLICATIONS

*Chemical Abstracts*, 96: 52154e (1982) [Viswanathan, N., et al., *Indian J. Chem.*, Sect. B. 1981, 20B(9), 776-779].

*Primary Examiner*—Richard A. Schwartz
*Attorney, Agent, or Firm*—Sprung Horn Kramer & Woods

[57] ABSTRACT

New isoindolin-2-yl-guanidines and isoindolin-2-yl-aminoimidazolines of the general formula

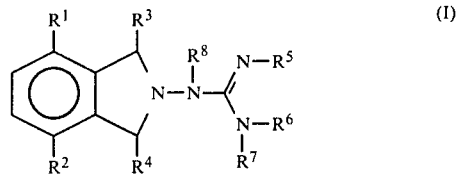

in which $R^1$ and $R^2$ can be identical or different and either hydrogen or a halogen, alkyl, or alkoxy, each with 1 to 4 carbon atoms, $R^3$ and $R^4$ can be identical or different and either a hydrogen or an alkyl with 1 to 4 carbon atoms, and $R^5$, $R^6$, $R^7$, and $R^8$ can be identical or different and either hydrogen or an alkyl with 1 to 4 carbon atoms, or in which $R^5$ and $R^6$ together represent the ethylene group, and their salts have an α-sympathomimetic and vasoconstrictive action that makes them appropriate as drugs for the treatment of hypotonic and rhinological states.

16 Claims, No Drawings

HYPERTENSIVE ISOINDOLIN-2-YL-AMINOIMIDAZOLINES AND ISOINDOLIN-2-YL-GUANIDINES

The objects of the invention are, first, new isoindolin-2-yl-guanidines and isoindolin-2-yl-aminoimidazolines of the general formula

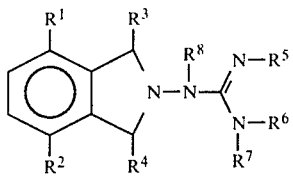

in which $R^1$ and $R^2$ can be identical or different and either hydrogen or a halogen, alkyl, or alkoxy, each with 1 to 4 carbon atoms, $R^3$ and $R^4$ can be identical or different and either a hydrogen or an alkyl with 1 to 4 carbon atoms, and $R^5$, $R^6$, $R^7$, and $R^8$ can be identical or different and either hydrogen or an alkyl with 1 to 4 carbon atoms or in which $R^5$ and $R^6$ together represent the ethylene group, second, their salts, except for 2-(N-aminoisoindolinyl)-imidazoline and 4-chloro-2-(2-imidazolin-2-ylamino)-isoindoline, third, a method of manufacturing them, fourth, drugs containing these compounds, and, fifth, the utilization of such drugs.

Isoindolinylimidazolines are known from German OS No. 2 816 627 and OS No. 2 905 501.

Preferred $R^1$ and $R^2$ residues are halogens, especially chlorine, methyl, ethyl, methoxy and ethoxy. The $R^3$, $R^4$, $R^5$, $R^6$, $R^7$ and $R^8$ residues are, in particular, methyl or ethyl. $R^8$ can also preferably be hydrogen.

The compounds in accordance with the invention, especially the imidazolines, preferably have one or, especially, two $R^3$ and $R^4$ and/or $R^1$ and $R^2$ substituents in each 1,3 and/or 4,7 position of the isoindoline.

1-Methyl-3-(4-chloroisoindolin-2-yl)-guanidine,
(1,3-dimethylisoindolin-2-yl)-guanidine,
(3-methyl-4-chloroisoindolin-2-yl)-guanidine,
(1,3-di-n-propylisoindolin-2-yl)-guanidine,
(1,2-diisopropylisoindolin-2-yl)-guanidine,
(4-chloro-7-methylisoindolin-2-yl)-guanidine,
4-bromo-7-methyl-2-(2-imidazolin-2-ylamino)-isoindoline,
4,7-di-n-propyl-2-(2-imidazolin-2-ylamino)-isoindoline,
4,7-diisopropyl-2-(2-imidazolin-2-ylamino)-isoindoline,
4,7-dibromo-2-(2-imidazolin-2-ylamino)-isoindoline,
4,7-dimethoxy-2-(2-imidazolin-2-ylamino)-isoindoline,
1,4-dimethyl-2-(2-imidazolin-2-ylamino)-isoindoline,
(4,7-dibromoisoindolin-2-yl)-guanidine,
4,7-dichloro-2-(2-imidazolin-2-ylmethylamino)-isoindoline,
4,7-dichloro-2-(2-imidazolin-2-yl-n-propylamino)-isoindoline,
2-(N-methylaminoisoindolinyl)-imidazoline, and
3-methyl-2-(2-imidazolin-2-ylmethylamino)-isoindoline
are examples of compounds with General Formula I that have a therapeutic action.

Isoindolinylaminoimidazolines with General Formula I in which $R^1$ and $R^2$ have the significance initially assigned to them except that at least one of them is not hydrogen and except that $R^2$ is not hydrogen when $R^1$ is chlorine, in which $R^3$, $R^4$, $R^7$, and $R^8$ are hydrogen, and in which $R^5$ and $R^6$ together represent the ethylene group are preferred.

Isoindolinylguanidines with General Formula I in which $R^1$, $R^2$, $R^3$, $R^4$, $R^7$, and $R^8$ have the initially assigned significance and in which $R^5$ and $R^6$ are hydrogen or an alkyl with 1 to 4 carbon atoms are also preferred.

Isoindolinylaminoimidazolines with General Formula I in which $R^1$, $R^2$, $R^3$, $R^4$, and $R^7$ have the initial significance, in which $R^5$ and $R^6$ together represent the ethylene group, in which $R^8$ is hydrogen, and in which at least one of the $R^3$, $R^4$, and $R^7$ substituents is an alkyl with 1 to 4 carbon atoms are also preferred.

Isoindolinylaminoimidazolines and isoindolinylguanidines of General Formula I in which $R^8$ is an alkyl group, especially the methyl group, with 1 to 4 carbon atoms and the other substituents have the initial significance are also preferred.

The compounds in accordance with the invention and their acid-addition salts have valuable therapeutic properties. They are especially distinguished by their long-lasting hypertensive action in cats and dogs. The doses employed with cats range from 0.1-1 mg/kg. The compounds are employed in dosages of 1-50 mg, especially, 1-5 mg per day to treat hypotensive states in warm blooded animals.

The substances in accordance with the invention can also, because of their α-sympathomimetic and vasoconstrictive action, be employed rhinologically, especially as nose drops in case of catarrh. At the preferred concentration of 0.1-1 mg/ml, which corresponds to a 0.01-0.1% aqueous solution, the preferred dosage of this form is several drops in each nostril several times a day.

It was impossible to predict that the compounds in accordance with the invention would have properties so outstanding in comparison with other compounds with similar structures. It must be assumed that the special and specific actions of these substances result from their particular structure.

It has been discovered, surprisingly, that replacing the isoindoline residues in either the 1,3 or the 4,7 position with substituents of the type described above transforms the hypotensive action of the 1,3- and 4,7-unsubstituted compounds (German OS No. 2 816 627 and OS No. 2 905 501) into a hypertensive action. The preponderantly α-sympatholytic action (German OS No. 2 816 627 and OS No. 2 905 501) of these drugs is also transformed when appropriate substitutions are made into an α-sympathomimetic and vasoconstrictive action.

1-Methyl-2-(2-imidazolin-2-ylamino)-isoindoline,
4,7-dimethyl-2-(2-imidazolin-2-ylamino)-isoindoline,
4-methyl-2-(2-imidazolin-2-ylamino)-isoindoline,
4,7-dichloro-2-(2-imidazolin-2-ylamino)-isoindoline,
(4,7-dimethylisoindolin-2-yl)-guanidine,
(4,7-dimethoxyisoindolin-2-yl)-guanidine,
(4,7-diethylisoindolin-2-yl)-guanidine,
(4-methylisoindolin-2-yl)-guanidine,
(4-chloroisoindolin-2-yl)-guanidine,
(1-methylisoindolin-2-yl)-guanidine, and
(4,7-dichloroisoindolin-2-yl)-guanidine
are especially preferred compounds, each of which has an especially powerful therapeutic action.

The invention can be employed to create pharmaceutical compositions that contain a compound with General Formula I or its pharmaceutically compatible salts along with a pharmaceutically compatible diluent or vehicle.

The compounds in accordance with the invention can be combined with conventional pharmaceutically compatible diluents or vehicles, and if necessary with other adjuvants, and administered orally or parenterally, for example. They can be administered orally in the form of tablets, capsules, syrups, suspensions, and liquids or parenterally in the form of solutions or suspensions. Orally administered preparations can contain one or more additives like sweeteners, flavorings, colorants, and preservatives. Tablets can contain the active ingredient mixed with such conventional pharmaceutically compatible adjuvants as inert diluents like calcium carbonate, sodium carbonate, lactose, and talc, granulating agents, agents like starch or alginic acid to promote disintegration when the tablets are taken orally, binders like starch or gelatine, and lubricants like magnesium stearate, stearic acid, and talc.

Milk sugar (lactose), gelatin, corn starch, stearic acid, ethanol, propylene glycol, tetrahydrofurfuryl alcohol ether, and water are appropriate vehicles.

The tablets can be coated by conventional methods to retard disintegration and absorption in the digestive tract to extend the action of the active ingredient. The active ingredient in a suspension can also be mixed with adjuvants conventionally employed in the manufacture of similar compositions, such as suspending agents like methyl cellulose, tragacanth, or sodium alginate, wetting agents like lecithin, poluethylene stearate, and polysorbate 80, and preservatives like ethylparaben. Capsules may contain the active ingredient alone or mixed with a solid diluent like calcium carbonate, calcium phosphate, or kaolin. The injectable preparations are also formulated by methods that are in themselves known. The pharmaceutical preparations can contain 0.1–90%, especially 1–90% of the active ingredient, with the remainder a vehicle or additive. Solid preparations like tablets and capsules are preferred from the aspect of manufacture and administration. Preparations intended for the treatment of hypotension will preferably contain 1–5 mg of active ingredient.

When employed for rhinological treatment, the preferred forms of the preparations are sprays and nose drops, to which conventional thickeners, additives, and preservatives can be added.

Methods of obtaining the compounds with General Formula I will now be described.

(a) Compounds with General Formula I in which $R^1$ to $R^8$ have the significance initially assigned to them can be obtained by converting compounds with the general formula

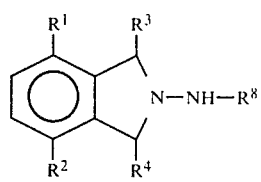

and with the significance initially assigned to $R^1$, $R^2$, $R^3$, $R^4$, and $R^8$ with a compound of the general formula

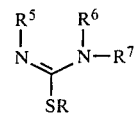

and with the significance initially assigned to $R^5$, $R^6$, and $R^7$, with R an alkyl, preferably a methyl.

Methylthio-compounds in the form of a hydrohalogenide, especially the hydroiodide, are especially appropriate. The conversion is conducted in an alcohol, n-amyl alcohol for instance, at the boiling point.

(b) Isoindolinylimidazolines with General Formula I, in which $R^7$ is hydrogen and in which $R^1$, $R^2$, $R^3$, $R^4$, and $R^8$ have the significance originally assigned to them can be obtained by converting compounds with the general formula

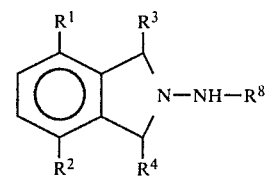

and with the significance initially assigned to $R^1$ to $R^4$ and $R^8$ with a compound with the general formula

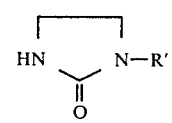

in which R' is an acyl group with 2 to 4 carbon atoms and by eliminating the acyl group.

The conversion is preferably conducted with a 1-acylimidazolidin-2-one in the presence of phosphorus oxychloride at temperatures of 100°–120° C. The acyl group can be eliminated with dilute acids at room temperature.

(c) Isoindolinylguanidines with General Formula I in which $R^1$ to $R^8$ have the significance originally assigned to them can be obtained by converting compounds with the general formula

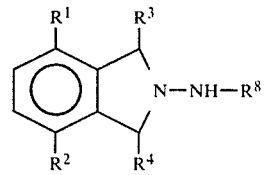

and with the significance initially assigned to $R^1$ to $R^4$ and $R^8$ with cyanamides.

The conversion is conducted in alcohols, preferably n-amyl alcohol, at the boiling point. Cyanamide leads to unsubstituted guanidines in which $R^5=R^6=R^7=H$, whereas the corresponding substituted cyanamides with $R^5$, $R^6$, and $R^7$ lead to the introduction of the substituents $R^5$, $R^6$, and $R^7$.

(d) Isoindolinylguanidines with General Formula I in which $R^1$ to $R^8$ have the significance originally assigned to them can also be obtained by reacting compounds with the general formula

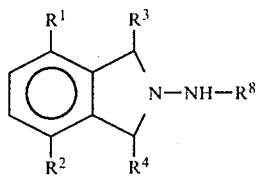

and with the significance initially assigned to $R^1$, $R^2$, $R^3$, $R^4$, and $R^8$ with aliphatic isothiocyanates with the formula $R^5NCS$ and with the significance initially assigned to $R^5$ into thiosemicarbazides with the general formula

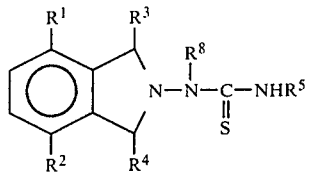

and with the significance initially assigned to $R^1$ to $R^5$ and $R^8$, by S-methylization with methyl iodide, and by converting with ammonia or with $R^6$- and $R^7$-substituted primary or secondary amines to introduce the $R^6$ and $R^7$ residues while eliminating the thio-substituents.

(e) Isoindolinylguanidines with General Formula I in which $R^1$, $R^2$, $R^3$, $R^4$, $R^6$, $R^7$, and $R^8$ have the significance originally assigned to them and $R^5$ is hydrogen can be obtained by converting compounds with the general formula

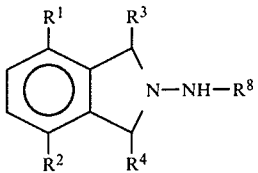

and with the significance initially assigned to $R^1$ to $R^4$ and $R^8$ with benzoyl isothiocyanate into thiosemicarbazides with the general formula

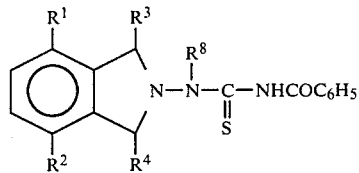

and by converting the thiosemicarbazides into compounds with the general formula

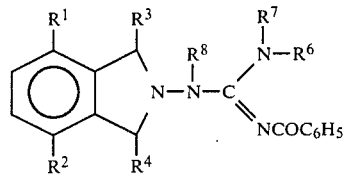

and with the significance initially assigned to $R^1$, $R^2$, $R^3$, $R^4$, $R^6$, $R^7$, and $R^8$ by reacting them with amines with the formula $R^6R^7NH$ with the significance initially assigned to $R^6$ and $R^7$ in the presence of mercury(II) oxide in an appropriate solvent like ethanol or water and methylene chloride.

The mercury(II) oxide can also be replaced with a salt of mercury like $Hg(OAc)_2$. Compounds with General Formula I can be obtained from compounds with General Formula VII by saponification with an aqueous solution of sodium or potassium hydroxide at the boiling point.

(f) Isoindolinylguanidines and imidazolines with General Formula I in which $R^1$ to $R^8$ have the significance originally assigned to them can be obtained by saponifying compounds with the general formula

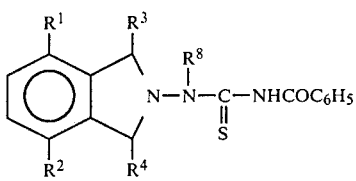

and with the significance initially assigned to $R^1$ to $R^4$ and $R^8$ with an aqueous solution of sodium or potassium hydroxide into thioureas with the general formula

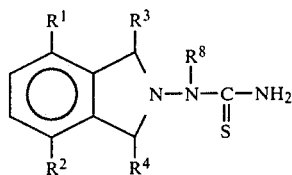

that are converted by alkylation, preferably by S-methylation with methyl iodide, into the S-alkylisothiuronium salts, which are then converted with $R^6$- and $R^7$-substituted primary or secondary amines into the guanidines in accordance with the invention or with ethylenediamine into the imidazolines in accordance with the invention.

The compounds with Formula II that are employed as starting materials are new. They can, like known compounds, be manufactured either from appropriately substituted phthalic anhydrides or xylene dihalogenides and t-butyl carbazate. They are valuable intermediate products for the manufacture of the final products in accordance with the invention.

These new starting products, the methods of manufacturing them, and their exploitation are also objects of the invention.

The compounds with General Formula I can be isolated as bases or in the form of their salts from the reaction mixtures.

They can be converted into salts by known methods with appropriate inorganic or organic acids. Physiologically compatible salts are preferred. Hydrohalic acids like hydrochloric acid or sulfuric acid are appropriate inorganic acids and fumaric acid and maleic acid are appropriate organic acids. The salts can be obtained by treating a hot alkaline solution of the base with an alcoholic solution of an appropriate acid and adding ethyl ether.

The invention will now be specified with reference to examples of some of its embodiments.

EXAMPLE 1

4,7-Dichloro-2-(2-imidazolin-2-ylamino)-isoindoline 5.9 g (0.025M) of 2-amino-4,7-dichloroisoindoline hydrochloride and 3,6 g (0.028M) of 1-acetylimidazolidin-2-one are heated to 100° C. over 2 hours in 50 ml of phosphorus oxychloride. The $Cl_3OP$ is evaporated off and the residue dissolved in 100 ml of ethanol and heated to the boiling point for 1 hour to eliminate the acetyl group. The solvent is drawn off in the vacuum, the residue picked up in water, alkalized with dilute sodium hydroxide solution, and extracted with chloroform. The chloroform is evaporated, and ethyl ether added, yielding 3.4 g of 4,7-Dichloro-2-(2-imidazolin-2-ylamino)-isoindoline as a base, which is converted with ethanolic hydrochloric acid into the hydrochloride.

Mp. 270°–272° C. (dec.)

EXAMPLE 2

4,7-Dimethyl-2-(2-imidazolin-2-ylamino)-isoindoline 4.4 g (0.031M) of benzoyl chloride in 10 ml of dimethoxyethane is dripped into a suspension of 2.5 g (0.033M) of ammonium thiocyanate in 50 ml of 1,2-dimethoxyethane. The mixture is stirred at room temperature for 1 hour. 4.5 g (0.028M) of 2-amino-4,7-dimethylisoindoline in 30 ml of dimethoxyethane are dripped in. The mixture is stirred at room temperature for 1 hour. The precipitated ammonium chloride is suctioned off. Evaporation yields 5.3 g of 1-benzoyl-3-(4,7-dimethylisoindolin-2-yl)-thiourea (Mp. 163°–164° C.) from the filtrate, which is converted by saponification with 50 ml of 10% sodium hydroxide into the (4,7-dimethylisoindolin-2-yl)-thiourea.

3.0 g of the thiourea are suspended in 50 ml of methyl alcohol and heated to the boiling point over 1 hour with 2.8 g of iodomethane. Conventional processing yields 4.2 g of S-methyl-N-(4,7-dimethylisoindolin-2-yl)-isothiuronium iodide.

Mp 181°–183° C.

4.0 g of the isothiuronium salt are suspended in 100 ml of n-amyl alcohol and reflux heated with 1.1 g of ethylenediamine for 20 minutes. The solvent is evaporated off and the residue distributed between chloroform and 2N of sodium hydroxide solution. The organic phase is dried and evaporated. Recrystallization from ethanol and ethyl acetate yields 1.6 g of 4,7-dimethyl-2-(2-imidazolin-2-ylamino)-isoindoline.

Mp. 205°–207° C.

Ethanolic hydrochloric acid yields 1.5 g of the hydrochloride of this compound.

Mp. 240°–242° C.

The following compounds are obtained by methods analagous to that employed in Example 2.

EXAMPLE 3

4-Methyl-2-(2-imidazolin-2-ylamino)-isoindoline

Mp. 143°–145° C.
Hydrochloride Fp. 210° C.

EXAMPLE 4

1-Methyl-2-(2-imidazolin-2-ylamino)-isoindoline

Mp. 136°–138° C.
Hydrochloride Fp. 198°–200° C.

EXAMPLE 5

(4,7-Dimethylisoindolin-2-yl)-guanidine 3.0 g (0.015M) of 4,7-dimethylisoindoline hydrochloride and 0.8 g (0.018M) of cyanamide are heated over 2 hours to the boiling point in 20 ml of n-amyl alcohol. The solvent is evaporated off and the residue recrystallized from isopropyl alcohol and ethyl ether, yielding 2.7 g of the (4,7-dimethylisoindolin-2-yl)-guanidine in the form of hydrochloride.

Mp. 196°–198° C. (dec.)

The following compounds (Formula I) are obtained by methods ananagous to that employed in Example 5.

| Ex. | $R^1$ | $R^2$ | $R^3$ | $R^4$ | $R^5$ | $R^6$ | $R^7$ | $R^8$ | Mp., °C. | Salt |
|---|---|---|---|---|---|---|---|---|---|---|
| 6 | $OCH_3$ | $OCH_3$ | H | H | H | H | H | H | 118–120 | HCl |
| 7 | $CH_3$ | H | H | H | H | H | H | H | 222–124 | HCl |
| 8 | $C_2H_5$ | $C_2H_5$ | H | H | H | H | H | H | 138 | HCL |
| 9 | Cl | Cl | H | H | H | H | H | H | 235–237 | HCL |
| 10 | Cl | H | H | H | H | H | H | H | 244–245 | HCl |
| 11 | H | H | $CH_3$ | H | H | H | H | H | 179–180 | HCl |
| 12 | H | H | $CH_3$ | $CH_3$ | H | H | H | H | | |
| 13 | H | H | $CH_3$ | H | H | $CH_3$ | $CH_3$ | H | 187–189 | HCl |
| 13a | H | H | H | H | H | H | $CH_3$ | H | 248 (dec.) | HCl |
| 13b | H | H | $CH_3$ | H | H | H | H | $CH_3$ | 240 (dec.) | HCl |

EXAMPLE 14

1,2-Dimethyl-3-(4,7-dimethylisoindolin-2-yl)-guanidine (a) 3.7 g (0.05M) of methyl isothiocyanate in 10 ml of dimethoxyethane is dripped into 8.0 g (0.05M) of 2-amino-4,7-dimethylisoindoline in 50 ml of 1,2-dimethoxyethane. Conventional processing was conducted after 15 hours, yielding 7.1 g of 1-methyl-3-(4,7-dimethylisoindolin-2-yl)-thiourea.

Mp. 177°–178° C.

(b) 3.0 g (0.013M) of thiourea prepared by the method followed in (a) and in 50 ml of methylene chloride is stirred for 3 hours at room temperature with 6.7 ml of a 40% aqueous methylamine solution and mercury oxide (from 7.1 g of $Cl_2Hg$ and aqueous NaOH). Following filtration, the organic phase was separated and evaporated and the residue taken up in dilute hydrochloric acid and extracted with ethyl acetate. The aqueous phase is evaporated. Recrystallization from ethyl acetate and ethanol yields 1.3 g of 1,2-dimethyl-3-(4,7-dimethylisoindolin-2-yl)-guanidine.

Mp. 230° C. (dec.)

The new intermediate products with General Formula II are obtained as follows.

EXAMPLE 15

2-Amino-4,7-dimethylisoindoline (a) 52.9 g (0.3M) of 3,6-dimethylphthalic anhydride in 300 ml of N,N-dimethylformamide are heated to the boiling point over 15 minutes with 46.3 g (0.35M) of t-butylcarbazate. Subsequent to evaporation of the solvent, 64 g of N-(t-butyloxycarbonylamino)-3,6-dimethylphthalimide are obtained from ethanol.

Mp. 187°–188° C. (Z).

(b) 63.9 g of N-(t-butyloxycarbonylamino)-3,6-dimethylphthalimide in 400 ml of absolute tetrahydrofuran are slowly dripped into a suspension of 20 g of aluminum lithium hydride in absolute tetrahydrofuran. The mixture is heated over 2 hours to the boiling point. Conventional processing yields 20 g of N-(t-butyloxycarbonylamino)-4,7-dimethylisoindoline.

Mp. 148°–151° C.

(c) 20 g of N-(t-butyloxycarbonylamino)-4,7-dimethylisoindoline are introduced into 200 ml of concentrated hydrochloric acid and stirred for 2 hours at room temperature. A yield of 17 g of the hydrochloride of 2-Amino-4,7-dimethylisoindoline precipitates in the form of crystals.

Mp. 185°–187° C.

The following 2-aminoisoindolines with General Formula II are obtained by methods similar to that in Example 15.

| Ex. | $R^1$ | $R^2$ | $R^3$ | $R^4$ | $R^8$ | Mp., °C. (HCl) |
|---|---|---|---|---|---|---|
| 16 | Cl | H | H | H | H | 205 (dec.) |
| 17 | Cl | Cl | H | H | H | 230–232 (dec.) |
| 18 | CH$_3$ | H | H | H | H | 210–211 (dec.) |
| 19 | OCH$_3$ | OCH$_3$ | H | H | H | 206 (dec.) |
| 20 | C$_2$H$_5$ | C$_2$H$_5$ | H | H | H | 176–178 |
| 21 | H | H | CH$_3$ | H | H | 152–153 |
| 21a | H | H | H | H | CH$_3$ | 168 |
| 21b | H | H | CH$_3$ | H | CH$_3$ | 152–153 |

EXAMPLE 22

The preparation of tablets

Tablets with the following components can be prepared by known methods. They can be employed in a dosage of 1–2 tablets 2 times per day to treat hypotension.

| | |
|---|---|
| 4,7-dimethyl-2-(2-imidazolin-2-ylamino)-isoindoline | 1.0 mg |
| lactose | 75.0 |
| corn starch | 10.0 |
| microcrystalline cellulose | 8.0 |
| povidone | 1.0 |
| magnesium stearate | 0.5 |
| Aerosil | 0.5 |

EXAMPLE 23

The preparation of ampuls

Ampuls with the following ingredients can be prepared by known methods. The active ingredients and the sodium chloride are dissolved in water and placed in the ampuls in a nitrogen atmosphere. They can be used in a dosage of 1–2 ampuls 2 times per day to treat hypotension.

| | |
|---|---|
| (4,7-dichloroisoindolin-2-yl)-guanidine | 1.0 mg |
| sodium chloride | 18.0 |
| distilled water ad 2 ml | |

EXAMPLE 24

The preparation of nose drops

Nose drops with the following ingredients can be prepared by known methods. They can be used in a dosage of 2–3 drops in each nostril 2–4 times per day.

| | |
|---|---|
| 1-methyl-2-(2-imidazolin-2-ylamino)-isoindoline | 0.1 g |
| methylcellulose | 1.0 g |
| distilled water ad 100 ml | |

What is claimed is:

1. An isoindolin-2-yl-guanidine or an isoindolin-2-yl aminoimidazoline of the formula $$\text{(I)}$$

in which $R^1$ and $R^2$ can be identical or different and are either hydrogen or a halogen, alkyl, or alkoxy, each with 1 to 4 carbon atoms, $R^3$ and $R^4$ can be identical or different and are either a hydrogen or an alkyl with 1 to 4 carbon atoms, and $R^5$, $R^6$, $R^7$, and $R^8$ can be identical or different and are either hydrogen or an alkyl with 1 to 4 carbon atoms, or in which $R^5$ and $R^6$ together represent the ethylene group, or a pharmaceutical by acceptable salt thereof, except for 2-(N-aminoisoindolinyl)-imidazoline and 4-chloro-2-(2-imidazolin-2-ylamino)-isoindoline.

2. An isoindolinylaminoimidazoline as in claim 1, with Formula I, in which Rr$^1$ and $R^2$ have the significance initially assigned to them except that at least one of them is not hydrogen and except that $R^2$ is not hydrogen when $R^1$ is chlorine, in which $R^3$, $R^4$, $R^7$, and $R^8$ are hydrogen, and in which $R^5$ and $R^6$ together represent the ethylene group.

3. An isoindolinylguanidine as in claim 1, with Formula I, in which $R^1$, $R^2$, $R^3$, $R^4$, $R^7$, and $R^8$ have the initially assigned significance and in which $R^5$ and $R^6$ are hydrogen or an alkyl with 1 to 4 carbon atoms.

4. An isoindolinylaminoimidazoline as in claim 1, with Formula I, in which $R^1$, $R^2$, $R^3$, $R^4$, and $R^7$ have the initial significance, in which $R^5$ and $R^6$ together represent the ethylene group, in which $R^8$ is hydrogen, and in which at least one of the $R^3$, $R^4$, and $R^7$ substituents is an alkyl with 1 to 4 carbon atoms.

5. An isoindolinylaminoimidazoline or isoindolinylguanidine as in claim 1, with Formula I, in which $R^8$ is an alkyl group, with 1 to 4 carbon atoms and the other substituents have the initial significance.

6. A compound of claim 5 in which $R^8$ is methyl.

7. A compound of claim 1 which is (4,7-dichloroisoindolin-2-yl)-guanindine or a pharmaceutically acceptable salt thereof.

8. A compound of claim 1 which is 4,7-dimethyl-2-(2-imidazolin-2-ylamino)-isoindoline or a pharmaceutically acceptable salt thereof.

9. A compound of claim 1 which is 1-methyl-2-(2-imidazolin-2-ylamino)-isoindoline.

10. A compound of claim 1 which is (4,7-dimethoxyisoindolin-2-yl)-guanidine.

11. A pharmaceutical composition comprising a hypertensively effective amount of a compound of claim 1 or a physiologically compatible acid-addition salt thereof together with an inert pharmaceutical carrier.

12. A pharmaceutical composition of claim 11 in oral unit dosage form.

13. A pharmaceutical composition comprising an amount of a compound of claim 1 or a physiologically compatible acid-addition salt thereof, effective for treating a rhinological state, together with an inert pharmaceutical carrier.

14. A pharmaceutical composition of claim 13 in the form of nose drops or sprays.

15. A method for the treatment of hypotension in a warm-blooded animal requiring said treatment which comprises administering to said warm-blooded animal a hypertensively effective amount of a compound of claim 1 or a physiologically compatible acid-addition salt thereof.

16. A method for the treatment of a rhinological state in a warm-blooded animal requiring said treatment which comprises administering to said warm-blooded animal an amount of a compound of claim 1 or a physiologically compatible acid-addition salt thereof, effective for treating said rhinological state.

* * * * *